United States Patent [19]
Kroll et al.

[11] Patent Number: 5,330,509
[45] Date of Patent: Jul. 19, 1994

[54] METHOD AND APPARATUS FOR FAR-FIELD TACHYCARDIA TERMINATION

[75] Inventors: Mark W. Kroll, Minnetonka; Theodore P. Adams, Edina, both of Minn.

[73] Assignee: Angeion Corporation, Plymouth, Minn.

[21] Appl. No.: 140,882

[22] Filed: Oct. 25, 1993

Related U.S. Application Data

[63] Continuation of Ser. No. 863,738, Apr. 6, 1992, abandoned.

[51] Int. Cl.⁵ .................................. A61N 1/362
[52] U.S. Cl. ......................................... 607/14
[58] Field of Search ................. 607/4, 5, 11, 14; 128/705, 696

[56] References Cited

U.S. PATENT DOCUMENTS

| | | | |
|---|---|---|---|
| 4,312,356 | 1/1982 | Sowton et al. | 128/419 |
| 4,390,021 | 6/1983 | Spurrell et al. | 128/419 |
| 4,398,536 | 8/1983 | Nappholz et al. | 128/419 |
| 4,403,614 | 9/1983 | Engle et al. | 607/5 |
| 4,408,606 | 10/1983 | Spurrell et al. | 128/419 |
| 4,488,554 | 12/1984 | Nappholz et al. | 128/419 |
| 4,799,493 | 1/1989 | Dufault | 128/705 |
| 4,996,984 | 3/1991 | Sweeney | 607/5 |
| 5,243,978 | 9/1993 | Duffin, Jr. | 607/11 |
| 5,247,929 | 9/1993 | Stoop et al. | 607/14 |

Primary Examiner—William E. Kamm
Attorney, Agent, or Firm—Patterson & Keough

[57] ABSTRACT

A method and apparatus provides a combination of an optimally short cardioversion pulse (about one millisecond in duration) followed by a train of largely conventional anti-tachycardia pacing pulses applied to pacemaker-catheter electrodes, for terminating ventricular tachycardia. Another embodiment delivers a train of anti-tachycardia pacing pulses through far-field electrodes, such as defibrillation electrodes. Still another embodiment delivers two or more optimally short pulses, closely spaced, through far-field electrodes, followed closely by a train of largely conventional anti-tachycardia pacing pulses. A closely related preferred embodiment comprises differing intervals between the far-field pulses and the subsequent pacing pulses. Apparatus of the present invention comprises an additional capacitor, smaller than the defibrillation capacitor and charged to a lower voltage, and better able to deliver pulses optimized for terminating ventricular tachycardia.

26 Claims, 4 Drawing Sheets

METHOD AND APPARATUS FOR FAR-FIELD TACHYCARDIA TERMINATION

This application is a continuation of Ser. No. 863,738 filed Apr. 6, 1994 and now abandoned.

BACKGROUND OF THE INVENTION

1. Field of the Invention

The present invention pertains to heart tachycardia, and more particularly, relates to ventricular tachycardia termination.

2. Description of the Prior Art

The basic concept of anti-tachycardia pacing was invented by Zacouto in the late 1960s. There have been many patents on traditional anti-tachycardia pacing. Examples are: U.S. Pat. No. 4,312,356 to Sowton; U.S. Pat. No. 4,390,021 to Spurrell; U.S. Pat. No. 4,398,536 to Nappholz; U.S. Pat. No. 4,408,606 to Spurrell; U.S. Pat. No. 4,488,554 to Nappholz; and U.S. Pat. No. 4,577,633 to Berkovitz.

No one has come close to the present concept of delivering multiple-pulse anti-tachycardia therapy through the defibrillation electrodes. Shenasa from Switzerland contributed an abstract at the American Heart Association meeting in 1991, Circ. Vol. 84, No. 4, p. II-426 (October, 1991 in which he applied very low voltages, under one volt, to defibrillation electrodes. He characterized these voltage as "sub-threshold stimulation" levels, and applied them at extremely high rates (50-millisecond pulses at the rate of 1200/minute). Shenasa's philosophy was to numb the myocardial cells near the electrodes in order to make these cells less likely to sustain the re-entrant loop of the ventricular tachycardia. He reported only a 52% success rate in treating tachycardia arrhythmias using this methodology. A U.S. Pat. No. 4,996,984, issued to Sweeney discloses the use of a pair (or more) of pulses for defibrillation. However, they were addressing fibrillation and not tachycardia. Also they were using pulses with just slightly less energy than conventional defibrillation pulses—on the order of 10 joules. Their work was inspired by the 20-year-old work of the Swedish researcher Kugelberg, who used trains of high-energy pulses to defibrillate.

In addition to the standard anti-tachycardia pacing of the prior art using the pacing electrodes on a standard cardiac catheter, there is another accepted technique for abolishing ventricular tachycardias. It is known as cardioversion, and involves the delivery of a single pulse through large-area defibrillation electrodes. Such a pulse usually has an energy in the neighborhood of one joule. This value is well above that of a pacing pulse, but far below that of a typical defibrillation pulse. While the present invention also uses defibrillation electrodes for terminating tachycardia, it is distinct from the prior art in using two or more pulses, and more wide-ranging energy values.

Figure 1:
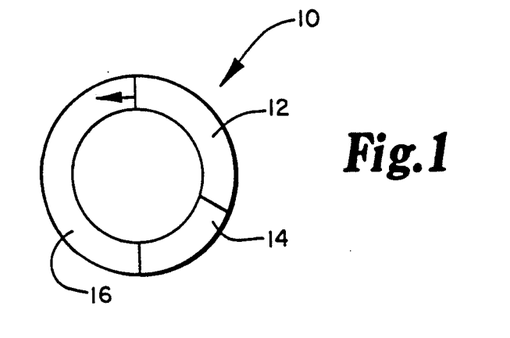

Ventricular tachycardia is a racing of the ventricle. The most accepted theory is that there exists a closed loop of myocardium with a diameter on the order of 1 cm, as illustrated in FIG. 1. That is, the path of cell stimulation is circular, with a path length (circumference) sufficient to permit a given cell to "repolarize", or to recover from the previous stimulation, before the wave of stimulation comes around the circle the next time. In biomedical terminology, such a closed loop is described as a "reentrant" loop, terminology that will be used below. The adjective generically identifies a situation wherein a path of adjacent-cell stimulation closes on itself, or "reenters" a previous path. In the loop case, the activated cells continue to activate cells in a counterclockwise rotation in continuous fashion. Immediately behind the cells just stimulated are cells that are fairly "refractory" or resistant to stimulation having not fully recovered from activation. Farther behind them are cells that are fully recovered (repolarized), and hence, are amenable to stimulation or reactivation.

This kind of "single-source" ventricular tachycardia generates a rather consistently shaped electrical signal, and hence, is referred to as a "monomorphic ventricular tachycardia". If there are more sources involved, then the arrhythmia is referred to as a "polymorphic ventricular tachycardia".

The presently accepted method of anti-tachycardia pacing is to pace at a remote location of the heart at a rate slightly higher than the ventricular tachycardia rate. The pacing pulse is delivered through conventional pacing electrodes that are essentially small point sources, a choice made to minimize the energy required to stimulate the closest neighboring cells. The activation pulse wave then spreads through the myocardium towards the re-entrant loop. It is desired that one of the pulses will arrive in the correct phase and will stimulate the cells of the loop that have recovered fully from activation. If this happens, then these cells will be refractory to the loop activation, and hence, the ventricular tachycardia will terminate.

This is weakly analogous to lighting a back-fire to stop a forest fire. The weakness in the analogy is that a forest fire does not repeatedly sweep the same area, and thus, does not give multiple opportunities for extinction or reignition.

Figure 2:
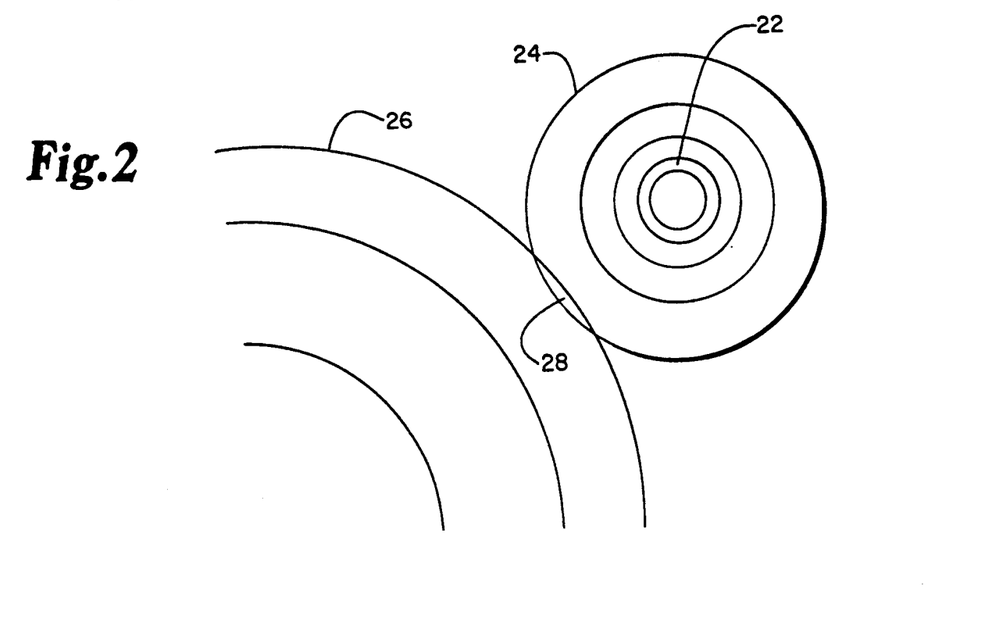
FIG. 2 illustrates the interaction and annihilation of a wave from a conventional anti-tachycardia pacing pulse by a wave from the reentrant loop.

There are several timing problems that prevent a 100% success rate with this technique. The major problem is that the pulse wave must arrive at the nearest side of the reentrant loop while it is in repolarization, or amenable to activation. Before it can do this, the wave must progress through myocardium without being annihilated by the activation waves emanating from the loop itself. (Recall that the loop is generating expanding activation waves throughout the myocardium in a fashion similar to the waves from a pebble dropped into the center of a smooth pond.) This problem is illustrated in FIG. 2. There is seen the wave at the lower left emanating from the pacing electrodes often one of the anti-tachycardia pulses was delivered. In an intermediate region, it competes with the wave launched by the reentrant loop responsible for the tachycardia, and has a fair probability of being annihilated.

The anti-tachycardia pacing of the prior art has been reported to work 50% to 90% of the time in cases of monomorphic ventricular tachycardia, with the chief problem being the critical timing constraints. This limited success in the prior art is bad enough, but the situation is actually worse. The series of pulses employed sometimes causes a higher-rate monomorphic ventricular tachycardia, or pulse-rate "acceleration". This can result in patient unconsciousness, or can require a painful high-energy shock for termination. Added to these problems for the monomorphic case, we must add that for cases of multiple loops (or sources), the prior art therapy has essentially no chance of working.

The prior art technique of anti-tachycardia pacing uses a burst of, for example, ten pulses at a rate slightly higher than the ventricular-tachycardia rate in hopes of abolishing it. Sometimes, pulse-rate "scanning" is employed in an effort to hit the correct rate. In scanning, the pacing valve is increased with every burst. In another prior art technique, "ramping" the rate is increased during the burst. The prior art chooses a higher rate of pacing because the pacing pulses will vary in phase with respect to the ventricular tachycardia, and thus, there is an increased opportunity for the pacing wave to arrive at a repolarized portion of the re-entrant loop before the pacing wave is itself annihilated.

The situation can be summarized in somewhat different words as follows. The high pulse rate in monomorphic tachycardia is a consequence of a signal circulating in a small-diameter closed loop at some location on the myocardium. The prior art therapy delivers a short series of pacing pulses at a rate higher than that of the tachycardia. The point of using the higher rate in therapy is so that as the wave launched by each therapeutic pulse arrives at the nearest edge of the loop, the chance of having such a wave's arrival coincide with having the repolarized (or stimulation-amenable) zone present at the nearest edge is increased; that is, one of the pulse waves from the short train will have a fair probability of arriving at just the right instant. (The geometrical situation can be appreciated from FIGS. 1 and 2.) Further, the point of using a burst of pulses, rather than a long series, is to provide a quiet interval after therapy during which dominance can be reestablished by waves coming from the pacemaker (whether from the heart's natural pacing center, or from the electrodes of a prosthetic pacemaker). The foregoing description explains the often indifferent results obtained using prior art anti-tachycardia methods, even in the simplest monomorphic case. The pulse waves may not arrive at the right time, may be annihilated by tachycardia waves, as in FIG. 2, and may induce even more serious conditions.

SUMMARY OF THE INVENTION

The general purpose of the present invention is to provide a new method of terminating ventricular tachycardia, involving the delivery of short, high-voltage pulses through large surface area defibrillation-style electrodes. The present invention is one preferred embodiment which delivers pulses of moderately high voltage through large-surface area electrodes for the control of tachycardia. A typical pulse would have an amplitude of 5 to 200 volts and a pulse duration of about 1 millisecond. The voltage is chosen to be high enough to stimulate a large portion of the heart directly, but without consuming high levels of energy. The pulse duration is chosen to approximate the chronaxie time for far-field stimulation of depolarized heart cells. This approximate match minimizes the delivered energy required per pulse. This, in turn, minimizes the amount of energy that must be replaced in the main capacitors. The timing of the pulses would be similar to the timing used in prior art anti-tachycardia pacing.

It is important for an appreciation of this invention, to understand the difference between pacing and far-field stimulation. In pacing, a low-voltage pulse is delivered into a small-surface-area electrode. This pulse "breaks down", or renders conductive, the membranes of a handful of neighboring cells so that they are activated (depolarized). These cells then stimulate more cells with which they are in direct contact. This cell-to-cell stimulation is not perfectly understood, but is thought to involve both ionic currents and capacitive coupling (displacement currents). The activation wave then moves through the heart of a velocity of about 100 cm/sec. An analogy is the lighting of a horizontal sheet of paper by igniting one corner. The corner is easy to ignite and the flame then spreads as an activation wave through the paper.

In far-field stimulation, an electric field of about 5 V/cm is generated within a region of the heart. The cylindrical heart cells (myocytes) are about 25 micrometers in diameter and 75 micrometers in length. The cells have a membrane with a thickness of about 8 nanometers. The field of 5 V/cm is parallel to the axis of the cell. The voltage drop along the length of the cell is now $V_d = (5 \text{ V/cm}) (75 \text{ um}) = 0.0375 \text{ V} = 37.5 \text{ mV}$. This hardly seems like enough voltage to break down a cell membrane that swings by 100 mV during depolarization. However, the insulating nature of the membrane, coupled with its conductive interior serves to concentrate this voltage drop through the membrane. Before membrane breakdown and cell activation, the internal cell potentials should be homogeneous. In other words, the membranes at each end of the cell must withstand the full voltage drop applied to the whole cell. Thus, each membrane end should see:

$$\frac{37.5 \text{ mV}}{2} = 18.75 \text{ mV} \qquad \text{Eq. 1}$$

for a field of $$E = \frac{18.75 \text{ mV}}{8 \text{ nm}} = 2,340,000 \text{ V/m} \qquad \text{Eq. 2}$$

which is a sufficient field to break down the membrane and begin the cell-activation process.

There is a subtle effect that can double this field. Instead of maintaining an isopotential cytoplasm (cell interior), the cell will try to minimize the internal field by redistributing charge. Another way of looking at this is that positive ions (mostly sodium) are attracted by the field toward the negatively charged electrode (cathode). This then increases the field across the membrane at the end where the positive sodium ions accumulate. A similar effect occurs with the negative chlorine ions at the opposite end.

Figure 3:
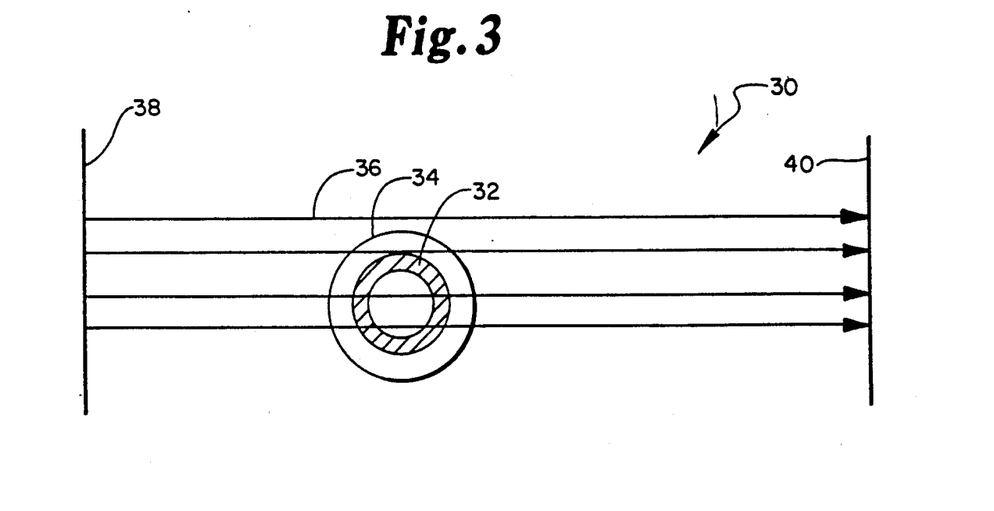
FIG. 3 illustrates the far-field stimulation of the present invention for tachycardia termination.

Thus, in far-field stimulation, the myocardial cells are simultaneously activated. This has a major advantage for dealing with monomorphic ventricular tachycardia, in that it removes (or at least minimizes) the timing problems of conventional anti-tachycardia pacing. This is because the far-field stimulation spreads not by activation of cells, but by electromagnetic wave propagation moving at a large fraction of the speed of light. This constitutes "simultaneous" stimulation as far as biological systems are concerned. More importantly, the far-field stimulation is not dependent on finding a path through unactivated (depolarized) cells. The desired stimulation spreads through electrical conduction, and not through cell-to-cell activation, which requires a path of cells that were not previously activated. This is illustrated in FIG. 3.

Hence, the far-field stimulation does not suffer from the two timing problems that seriously limit the effectiveness of prior art anti-tachycardia pacing. First, it is not annihilated by activation waves emanating from the loop; and second, it need not first make contact with the reentrant loop at a repolarized section.

It is important to note that the far-field stimulation not be so strong as to stimulate the whole heart. If the strength of the pulses is sufficient to stimulate directly only, say, 50% of the heart then there is still a much increased chance of terminating the ventricular tachycardia. If the generating loop is within the stimulated 50%, then the tachycardia will probably be terminated. If the loop is outside of this region, then the far-field stimulation still has a much improved chance of termination since there are more and broader pathways for delivering the stimulation to the loop.

Figure 4:
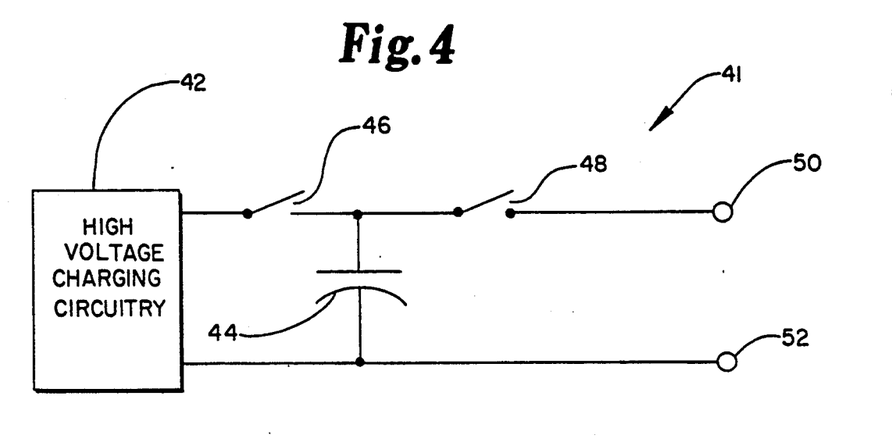
FIG. 4 illustrates schematically a circuit used for generating both defibrillation pulses and the anti-tachycardia pulses of the present invention.

There are many ways to deliver the far-field stimulation pulses to the electrodes. One technique is to use the main (defibrillation) capacitor in an implantable cardioverter defibrillator (ICD), charging it up to a limited voltage (5 to 200 volts) and delivering a short (about 1 millisecond) pulse from that capacitor. This option is illustrated in FIG. 4. The advantage of this approach is that no additional capacitors are needed.

Figure 5:
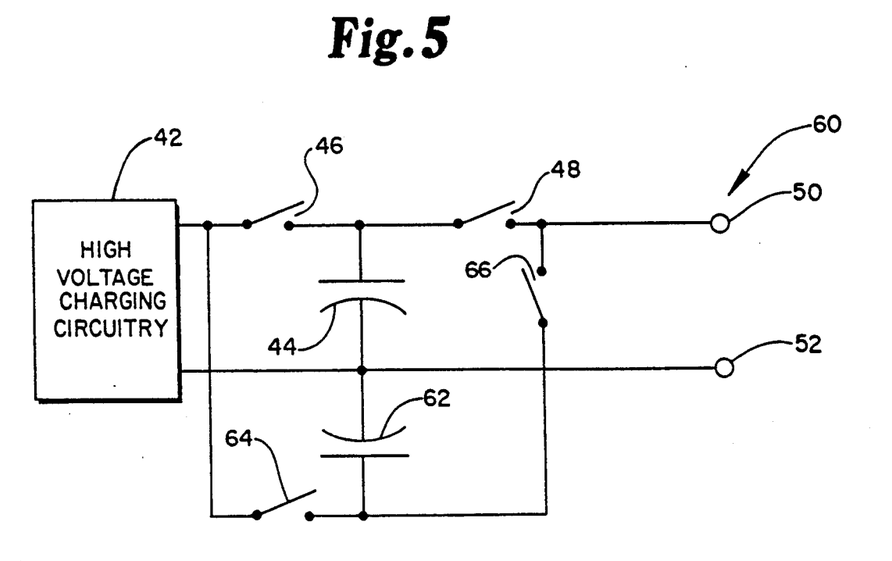
FIG. 5 illustrates schematically a circuit of the present invention used for generating defibrillation pulses with one capacitor and the anti-tachycardia pulses with an additional capacitor optimized for the purpose; and, FIG. 6 illustrates the placement and configuration of alternative embodiments of the electrodes of a preferred embodiment of the present invention.

Another technique would be to use a separate smaller capacitor to deliver the far-field stimulation pulses. The advantage of this approach is that the additional capacitor may be charged to a lower voltage than that of the main capacitor. This would allow the main capacitor to be charged to a full voltage as a backup measure in case the far-field stimulation accelerated the tachycardia. This additional capacitor value may also be chosen to deliver pulses of more energy efficiency to the heart. For example, the additional capacitor could have a value of some 15 to 20 microfarads, which is a small value compared to those of typical defibrillation capacitors. The two-capacitor option is illustrated in FIG. 5. There, the switch 46 is closed to charge the capacitor 44 for delivery of a conventional defibrillation pulse. Here, switch 46 is opened to isolate the defibrillation capacitor 44, and then the switch 48 is closed to deliver the defibrillation pulse to the heart. The smaller and additional anti-tachycardia capacitor 62, on the other hand, is charged by closing switch 64. After that, switch 64 is opened to isolate capacitor 62, and then switch 66 is closed to deliver an anti-tachycardia pulse to the same electrodes as before.

Other preferred embodiments of the present invention also exist. In each of them, the one-capacitor or the novel two-capacitor apparatus may be used to deliver the desired pulses. In the first of these additional preferred embodiments, a high-voltage anti-tachycardia pulse is delivered to the far-field electrodes, with the interval between it and the last preceding pulse from the tachycardial malfunction being shorter than the intervals between the train of tachycardia pulses. The high-voltage pulse is then followed by a train of ten or fewer pacing pulses delivered to the pacing electrodes of a cardiac catheter, with the interval between the first of these and the high-voltage pulse, as well as their mutual intervals being at least as short as the first-specified interval.

The next preferred embodiment of the present invention employs two high-voltage pulses in place of one. The interval between the two high-voltage pulse is the same as the first-specified interval in the previous embodiment, and the subsequent intervals are specified the same as those in the previous embodiment. The last preferred embodiment is like the one just described, except that the interval between the two high-voltage pulses is different from the intervals that follow.

One significant aspect and feature of the present invention is the delivery for tachycardia termination of at least two short, high-voltage electrical pulses through far-field electrodes.

Another significant aspect and feature of the present invention is the delivery for tachycardia termination of at least two short, high-voltage electrical pulses through electrodes, wherein the combined surface area of the far-field electrodes exceeds one square centimeter.

An additional significant aspect and feature of the present invention is the delivery for tachycardia termination of at least two short, high-voltage electrical pulses through defibrillation electrodes.

A further significant aspect and feature of the present invention is the delivery for tachycardia termination of at least two short, high-voltage electrical pulses each having an energy value between 0.01 joule and 5 joules.

A still further significant aspect and feature of the present invention is the delivery for tachycardia termination of at least two short, high-voltage electrical pulses each having a duration of less than 3 milliseconds.

Another significant aspect and feature of the present invention is the delivery for tachycardia termination of at least two short, high-voltage electrical pulses each having an amplitude between 5 volts and 200 volts.

Another significant aspect and feature of the present invention is the delivery for tachycardia termination of fewer than ten short, high-voltage electrical pulses through far-field electrodes.

Another significant aspect and feature of the present invention is the delivery for tachycardia termination of at least two short, high-voltage electrical pulses delivered from the defibrillation capacitor.

Another significant aspect and feature of the present invention is the delivery for tachycardia termination of at least two short, high-voltage electrical pulses delivered from an additional capacitor smaller than the defibrillation capacitor.

Another significant aspect and feature of the present invention is the delivery for tachycardia termination of at least two short, high-voltage electrical pulses delivered from a capacitor of less than 15 microfarads.

Another significant aspect and feature of the present invention is the delivery of a single short, high-voltage electrical pulse through far-field electrodes at an interval following a tachycardia pulse that is shorter than the interval between tachycardia pulses, said high-voltage pulse followed by at least ten pacing pulses, delivered through pacemaker electrodes, that are spaced from the high-voltage pulse and from each other by intervals at least as short as that between the high-voltage pulse and the preceding tachycardia pulse.

Another significant aspect and feature of the present invention is the delivery of a single short, high-voltage electrical pulse through far-field electrodes at an interval following a tachycardia pulse that is shorter than the interval between tachycardia pulses, said high-voltage pulse followed by at least ten pacing pulses, delivered through pacemaker electrodes, that are spaced from the high-voltage pulse and from each other by intervals at least as short as that between the high-voltage pulse and the preceding tachycardia pulse.

Another significant aspect and feature of the present invention is the delivery for tachycardia termination of a single short, high-voltage electrical pulse through far-field electrodes at an interval following a tachycardia pulse that is shorter than the interval between tachycardia pulses, said high-voltage pulse followed by at least ten pacing pulses, delivered through pacemaker electrodes, that are spaced from the high-voltage pulse and from each other by intervals at least as short as that between the high-voltage pulse and the preceding tachycardia pulse.

Another significant aspect and feature of the present invention is the delivery for tachycardia termination of at least two short, high-voltage electrical pulses through far-field electrodes at an interval following a tachycardia pulse that is shorter than the interval between tachycardia pulses, said high-voltage pulses separated by an interval at least as short as that between the first high-voltage pulse and the preceding tachycardia pulse, and with the second high-voltage pulse followed by at least ten pacing pulses, delivered through pacemaker electrodes, that are spaced from the high-voltage pulse and from each other by intervals at least as short as that between the high-voltage pulses.

Another significant aspect and feature of the present invention is the delivery for tachycardia termination of two short, high-voltage electrical pulses through far-field electrodes at an interval following a tachycardia pulse that is shorter than the interval between tachycardia pulses, said high-voltage pulses separated by an interval at least as short as that between the first high-voltage pulse and the preceding tachycardia pulse, and with the second high-voltage pulse followed by at least ten pacing pulses, delivered through pacemaker electrodes, that are spaced from the high-voltage pulse and from each other by intervals that are different from that between the high-voltage pulses.

Having thus described embodiments and features of the present invention, it is a principal object of the present invention to achieve the termination of tachycardia more effectively than permitted by the methods of the prior art.

One object of the invention is delivery of a train of anti-tachycardia pulses through far-field electrodes, such as defibrillation electrodes.

Another object of the invention is to use for terminating tachycardia novel combinations of prior-art elements, such as one or more cardioversion pulses followed by anti-tachycardia pacing pulses.

A further object of the invention is to employ pulses high in voltage but low in energy for "pacing through defibrillation electrodes," thus conserving battery energy while optimizing the anti-tachycardia therapy.

A still further object of the invention is to use for terminating tachycardia novel combinations of novel elements and prior-art elements, such as pacing through defibrillation electrodes with optimized pulses shorter than conventional cardioversion pulses, with and without subsequent conventional anti-tachycardia pacing pulses.

A still further object of the invention is to employ one or more cardioversion pulses of optimum duration, and to follow such a pulse or pulses by conventional anti-tachycardia pacing pulses.

A still further object of the invention is to employ an additional capacitor for cardioversion that is smaller than a defibrillation capacitor, and that can therefore deliver the short pulse or pulses of the present invention more efficiently than can a defibrillation capacitor.

A still further object of the invention is to provide a circuit for charging and discharging the additional and smaller capacitor of the present invention.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

FIG. i illustrates the reentrant loop of cells that enters into a widely accepted theory of ventricular tachycardia.

DETAILED DESCRIPTION OF THE DRAWINGS

FIG. 1 illustrates a reentrant loop 10 of cells of the myocardium that enters into a widely accepted theory of ventricular tachycardia, the loop including in sequence activated cells 12, refractory cells that have not yet recovered from activation, and repolarized cells 16 that can again be activated.

FIG. 2 illustrates schematically the geometrical pattern 20 of the interaction of a reentrant loop 22 having a wave such as 24 interacting with a wave such as 26 that is emanating from the pacing electrodes of a conventional catheter in the conventional anti-tachycardia pacing therapy, with wave annihilation occurring in the region 28.

FIG. 3 illustrates schematically the geometrical pattern 30 of the stimulation of a reentrant loop 32 with a wave 34 emanating from it, by an electric field represented by lines of force such as 36, said electric field produced by far-field electrodes 38 and 40 in accordance with the present invention, and being relatively unaffected by the wave 34.

FIG. 4 illustrates schematically a circuit 41 used for generating both defibrillation pulses and the anti-tachycardia pulses of the present invention, including a high-voltage circuitry 42 that charges capacitor 44 when switch 46 is closed; when switch 46 is subsequently opened, the capacitor 44 is isolated and can then be discharged by closing switch 48, thus delivering an energetic defibrillation pulse to cardiac electrodes 50 and 52. In a similar way, the capacitor 44 can be charged to a lower voltage and then discharged to deliver one or more lower-energy cardioversion pulses to the heart, or two or more anti-tachycardia pacing pulses of the present invention to the heart.

FIG. 5 illustrates schematically a circuit 60 of the present invention used for generating both defibrillation pulses and the anti-tachycardia pulses of the present invention, including high-voltage circuitry 42 that charges defibrillation capacitor 44 when switch 46 is closed; when switch 46 is subsequently opened, the capacitor 44 is isolated and can then be discharged by closing switch 48, thus delivering an energetic defibrillation pulse to cardiac electrodes 50 and 52. In a similar way, the smaller anti-tachycardia capacitor 62 can be charged to a lower voltage by closing switch 64 and then discharged after opening switch 64 by closing switch 66 to deliver an optimized lower-energy cardioversion pulse to the heart, a process that can be repeated to deliver two or more such pulses, or to deliver two or more optimized anti-tachycardia pacing pulses of the present invention to the heart.

Figure 6:
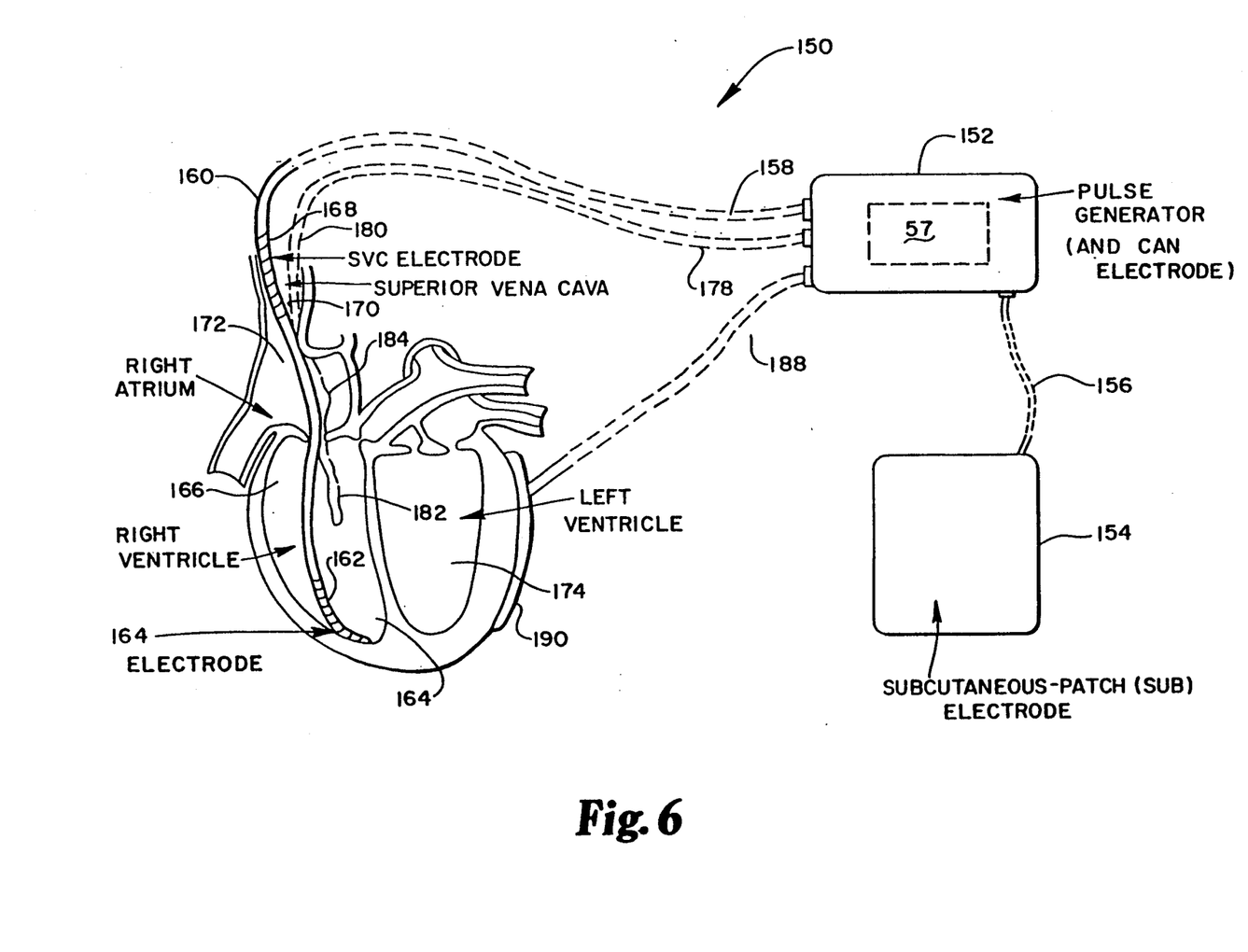

FIG. 6 illustrates schematically and for purposes of illustration a defibrillation system 150 including a subcutaneously implanted ICD or pulse generator 157 optionally serving as a CAN electrode 152. In the embodiment shown in FIG. 6, the pulse generator 157 is attached to a subcutaneously implanted SUB electrode 154 by interconnection lead 156, by interconnection lead 158 to a cardiac defibrillation-style catheter 160, by interconnection lead 178 to a cardiac pacing-style catheter 180, and by interconnection lead 188 to an epicardial patch electrode 190. The defibrillation-style catheter 160 includes a first endocardial-coil electrode 162 positioned at the apex 164 of the right ventricle 166, the coil being the RVA electrode 162, and a second endocardial-coil electrode 168 positioned in the superior vena cava 170, which is above the right atrium 172, the second coil being the SVC electrode 168. The pacing-style catheter 180 includes a first proximal 184 and a second distal electrodes 182. It will be seen from this figure that the electrodes 162 and 168 of the far-field defibrillation-style catheter are relatively larger in surface area, having a total surface area of greater than about 1 cm² and are positioned closely together. In contrast to the far-field electrodes 162 and 168 of the defibrillation-style catheter, the electrodes 184 and 182 of the pacing-style catheter have relatively small surface areas, generally less than about 1 cm² and are positioned much further away from each other. In addition to the use of the electrodes 162 and 168 on the defibrillation-style catheter 160 as the far-field electrodes, the ICD can also use a configuration that causes the stimulation pulse current coming from the CAN electrode 152 and coming from the SUB electrode 154 to substantially to intersect the left ventricle 174, as well as the right ventricle 166. Another alternative is to use one or more epicardial patch electrodes 190 as one or more the far-field electrodes.

Figure 7:
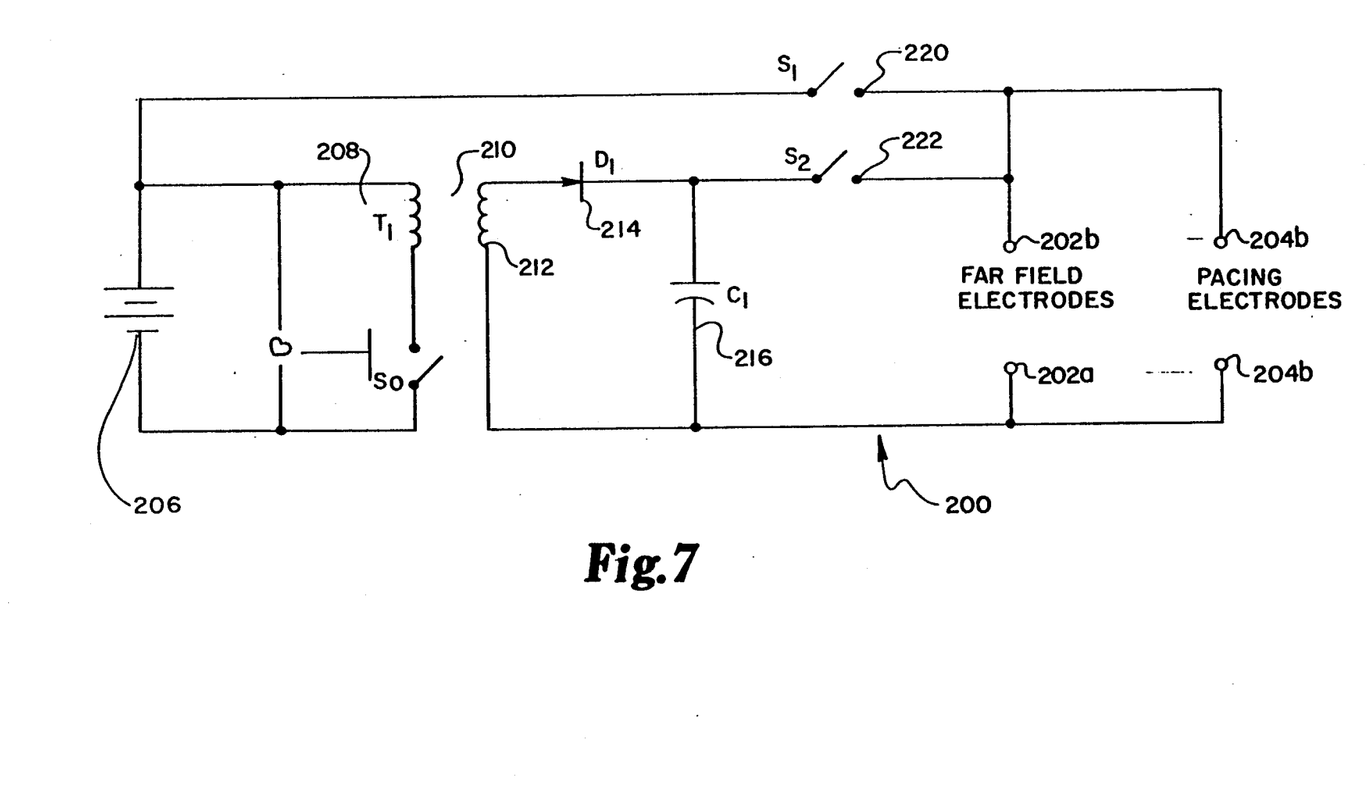
FIG. 7 illustrates schematically a circuit used to produce the stimulation pulse series in an embodiment of the present invention that utilizes both far-field electrodes and pacing electrodes.

FIG. 7 shows schematically a circuit 200 used to produce the stimulation pulse series in an embodiment of the present invention that utilizes both far-field electrodes 202a, 202b and pacing electrodes 204a, 204b. A battery 206 is used to supply current to the primary coil 208 of transformer 210. The secondary coil 212 of the transformer 210 produces a fly-back voltage which is rectified by diode 214 and stored in capacitor 216. For delivery of conventional pacing pulses, switch 220 is enabled which delivers a battery voltage (nominal 6 volt) to the pacing electrodes 204a, 204b. If switch 222 is enabled, it delivers the high voltage present on capacitor 216 to the far-field electrodes 202a, 202b. It will be appreciated that the capacitor of the present invention can be either a single capacitor, or a combination of capacitors having an effective capacitance required to store the necessary energy for the cardioversion pulses and defibrillation countershocks. Similarly, it will also be appreciated that the voltage of the pacing pulses can be doubled using a simple voltage doubler circuitry.

MODE OF OPERATION

The present invention comprises in part a novel combination of conventional techniques for terminating ventricular tachycardia. In one case, a cardioversion pulse is followed by largely conventional anti-tachycardia pacing pulses. In a related case, the cardioversion pulse is shortened to an optimal degree (to about one millisecond), and is followed closely by essentially conventional pacing pulses. In a different preferred embodiment, high-voltage and optimally short pulses are delivered as pacing pulses through far-field electrodes such as defibrillation electrodes. In yet another embodiment, these are followed by largely conventional pacing pulses. Still another embodiment employs differing intervals between the high-voltage pulses and the pacing pulses. A new apparatus of the present invention provides for the charging and discharging of a capacitor in addition to and considerably smaller than a typical defibrillation capacitor, for the purpose of delivering optimized pacing or cardioversion pulses through far-field electrodes.

Various modifications can be made to the present invention without departing from the apparent scope hereof.

We claim:

1. A method for operating an implantable device connected to at least two implanted electrodes located in a human patient to treat ventricular tachycardia, the method comprising the device-implemented steps of:
    (a) sensing a ventricular tachycardia in the human patient; and
    (b) in response to the ventricular tachycardia, delivering a series of two or more anti-tachycardia electrical stimulation pulses each having an energy value of less than about 5 joules to the two or more electrodes in a committed burst of less than about 5 seconds, at least one of the stimulation pulses being a far-field pulse having an energy value between about 0.01 joule and 5 joules, an amplitude between about 5 volts and 200 volts, and being delivered through two or more far-field electrodes having a combined surface area that exceeds about 1 square centimeter and an inter-electrode distance of greater than about 2 centimeters.

2. The method of claim 1 wherein the far-field pulses each have a duration of less than about 5 milliseconds.

3. The method of claim 1 wherein more than one burst of the series of stimulation pulses are used to treat the ventricular tachycardia.

4. The method of claim 1 wherein the total number of stimulation pulses in the burst is less than about ten.

5. The method of claim 1 wherein the ventricular tachycardia is sensed as a continuous sequence of intrinsic ventricular tachycardial contractions having a rate of between 150-240 bpm.

6. The method of claim 1 wherein the far-field pulses are delivered from a capacitor which does not store electrical energy for a defibrillation countershock pulse, the capacitor having an effective capacitance of less than about 15-20 microfarads.

7. The method of claim 1 wherein a first pulse in the series of stimulation pulses is a far-field pulse and all subsequent pulses in the series of stimulation pulses are pacing pulses delivered through two or more pacing electrodes having a combined surface area of less than about 1 square centimeter and an inter-electrode distance of less than about 2 centimeters.

8. The method of claim 1 wherein the ventricular tachycardia is sensed as a continuous sequence of intrinsic ventricular tachycardial contractions, and wherein the first pulse is delivered at an interval following a ventricular tachycardial contraction that is shorter than an interval between sequential ventricular tachycardial contractions and the subsequent stimulation pulses are spaced from the first pulse and from each other by intervals at least as short as that between the first pulse and the preceding ventricular tachycardial contraction.

9. The method of claim 1 wherein the ventricular tachycardia is sensed as a continuous sequence of intrinsic ventricular tachycardial contractions, and wherein a first and second pulse in the series of stimulation pulses are far-field pulses delivered at an interval following a ventricular tachycardial contraction that is shorter than the interval between ventricular tachycardial contractions, the first and second far-field pulses being separated by an interval at least at least as short as that between the first pulse and the preceding ventricular tachycardial contraction, and the second pulse being followed by a short train of pacing pulses delivered through two or more pacing electrodes having a combined surface area of less than about 1 square centimeter and an inter-electrode distance of less than about 2 centimeters, the short train of pacing pulses being spaced from the first and second far-field pulses and from each other by intervals at least as short as that between the first and second far-field pulses.

10. The method of claim 1 wherein the ventricular tachycardia is sensed as a continuous sequence of intrinsic ventricular tachycardial contractions, and wherein a first and second pulse in the series of stimulation pulses are far-field pulses delivered at an interval following a ventricular tachycardial contraction that is shorter than the interval between ventricular tachycardial contractions, the first and second far-field pulses being separated by an interval at least as short as that between the first pulse and the preceding ventricular tachycardial contraction, and the second pulse being following by a short train of pacing pulses delivered through two or more pacing electrodes having a combined surface area of less than about 1 square centimeter and an inter-electrode distance of less than about 2 centimeters, the short train of pacing pulses being spaced from the first and second far-field pulses and from each other by intervals that are different from that between the first and second far-field pulses.

11. The method of claim 1 wherein the ventricular tachycardia is sensed as a continuous sequence of intrinsic ventricular tachycardial contractions, and wherein a first pulse in the series of stimulation pulses is a conventional cardioversion pulse and the subsequent pulses in the series of stimulation pulses are conventional anti-tachy pacing pulses delivered without any intervening monitoring of the ventricular tachycardial contractions after an interval that is shorter than the interval between ventricular tachycardial contractions.

12. The method of claim 1 wherein the ventricular tachycardia is sensed as a continuous sequence of intrinsic ventricular tachycardial contractions, and wherein a first pulse in the series of stimulation pulses is a conventional cardioversion pulse having a pulse duration of less than about 5 msec and the subsequent pulses in the series of stimulation pulses are conventional anti-tachy pacing pulses delivered without any intervening monitoring of the ventricular tachycardial contractions.

13. An implantable apparatus for treating ventricular tachycardia in a human patient, comprising:
two or more implanted electrodes, including at least a pair of far-field electrodes having a combined surface area that exceeds about 1 square centimeter and an inter-electrode distance of greater than about 2 centimeters;
means for sensing a ventricular tachycardia in the human patient; and
means for delivering a series of two or more anti-tachycardia, electrical stimulation pulses in reponse to the ventricular tachycardia, each stimulation pulse having an energy value of less than about 5 joules to the two or more electrodes in a committed burst of less than about 5 seconds, at least one of the stimulation pulses being a far-field pulse delivered through the far-field electrodes and having an energy value between about 0.01 joule and 5 joules and an amplitude between about 5 volts and 200 volts.

14. The implantable apparatus of claim 13 wherein the means for delivering a series of stimulation pulses comprises:
capacitor means for storing a preselected amount of electrical energy for at least the far-field pulses;
high voltage charging circuit means for charging the capacitor means to the preselected amount of electrical energy;
switch means for selectively controlling a time-truncated discharge of the capacitor means through the far-field electrodes in response to the ventricular tachycardia to produce the stimulation pulses.

15. The implantable apparatus of claim 14 further comprising:
at least a pair of pacing electrodes having a combined surface area less than about 1 square centimeter and an inter-electrode distance of less than about 2 centimeters; and
power source means operably connected to said switch means for directly producing one or more pacing pulses each having an energy value of less than about 100 $\mu$joules to be delivered through the pacing-style electrodes as part of the series of stimulation pulses.

16. The implantable apparatus of claim 13 wherein the far-field pulses each have a duration of less than about 5 milliseconds.

17. The implantable apparatus of claim 13 wherein more than one burst of the series of stimulation pulses are used to treat the ventricular tachycardia.

18. The implantable apparatus of claim 13 wherein the total number of stimulation pulses in the burst is less than about ten.

19. The implantable apparatus of claim 13 wherein the ventricular tachycardia ia sensed as a continuous sequence of intrinsic ventricular tachycardial contractions having a rate of between 150-240 bpm.

20. The implantable apparatus of claim 13 wherein the far-field pulses are delivered from a capacitor which does not store electrical energy for a defibrillation countershock pulse, the capacitor having an effective capacitance of less than about 15-20 microfarads.

21. The implantable apparatus of claim 13 wherein a first pulse in the series of stimulation pulses is a far-field pulse and all subsequent pulses in the series of stimulation pulses are pacing pulses delivered through two or more pacing electrodes having a combined surface area of less than about 1 square centimeter and an inter-electrode distance of less than about 2 centimeters.

22. The implantable apparatus of claim 13 wherein the ventricular tachycardia is sensed as a continuous sequence of intrinsic ventricular tachycardial contractions, and wherein the first pulse is delivered at an interval following a ventricular tachycardial contraction that is shorter than an interval between sequential ventricular tachycardial contractions and the subsequent stimulation pulses are spaced from the first pulse and from each other by intervals at least as short as that between the first pulse and the preceding ventricular tachycardial contraction.

23. The implantable apparatus of claim 13 wherein the ventricular tachycardia is sensed as a continuous sequence of intrinsic ventricular tachycardial contractions, and wherein a first and second pulse in the series of stimulation pulses are far-field pulses delivered at an interval following a ventricular tachycardial contraction that is shorter than the interval between ventricular tachycardial contractions, the first and second far-field pulses being separated by an interval at least as short as that between the first pulse and the preceding ventricular tachycardial contraction, and the second pulse being followed by a short train of pacing pulses delivered through two or more pacing electrodes having a combined surface area of less than about 1 square centimeter and an inter-electrode distance of less than about 2 centimeters, the short train of pacing pulses being spaced from the first and second far-field pulses and from each other by intervals at least as short as that between the first and second far-field pulses.

24. The implantable apparatus of claim 13 wherein the ventricular tachycardia is sensed as a continuous sequence of intrinsic ventricular tachycardial contractions, and wherein a first and second in the series of stimulation pulses are far-field pulses delivered at an interval following a ventricular tachycardial contraction that is shorter than the interval between ventricular tachycardial contractions, the first and second far-field pulses being separated by an interval at least as short as that between the first pulse and the preceding ventricular tachycardial contraction, and the second pulse being followed by a short train of pacing pulses delivered through two or more pacing electrodes having a combined surface area of less than about 1 square centimeter and an inter-electrode distance of less than about 2 centimeters, the short train of pacing pulses being spaced from the first and second far-field pulses and from each other by intervals that are different from the between the first and second far-field pulses.

25. The implantable apparatus of claim 13 wherein the ventricular tachycardia is sensed as a continuous sequence of intrinsic ventricular tachycardial contractions, and wherein a first pulse in the series of stimulation pulses is a conventional cardioversion pulse and the subsequent pulses in the series of stimulation pulses are conventional anti-tachy pacing pulses delivered without any intervening monitoring of the ventricular tachycardial contractions after an interval that is shorter than the interval between ventricular tachycardial contractions.

26. The implantable apparatus of claim 13 wherein the ventricular tachycardia is sensed as a continuous sequence of intrinsic ventricular tachycardial contractions, and wherein a first pulse in the series of stimulation pulses is a conventional cardioversion pulse having a pulse duration of less than about 5 msec and the subsequent pulses in the series of stimulation pulses are conventional anti-tachy pacing pulses delivered without any intervening monitoring of the ventricular tachycardial contractions.

* * * * *